United States Patent [19]

Wright

[11] Patent Number: 4,539,422
[45] Date of Patent: Sep. 3, 1985

[54] PROCESS FOR PREPARING CEPHALOSPORIN INTERMEDIATES

[75] Inventor: Ian G. Wright, Greenwood, Ind.

[73] Assignee: Eli Lilly and Company, Indianapolis, Ind.

[21] Appl. No.: 704,234

[22] Filed: Feb. 22, 1985

Related U.S. Application Data

[63] Continuation of Ser. No. 534,467, Sep. 21, 1983, abandoned.

[51] Int. Cl.³ .............................................. C07C 69/003
[52] U.S. Cl. .................................................... 560/155
[58] Field of Search ......................................... 560/155

[56] References Cited

U.S. PATENT DOCUMENTS 3,962,272  6/1976  Katner ................................. 548/253
4,174,347 11/1979 Austermühle-Bertola ..... 260/464 X

OTHER PUBLICATIONS

Childs et al.; *J. Org. Chem.*, 41 (No. 21), 1976, pp. 3486 and 3487, Preparation of Cyanoformates, Crown Ether Phase Transfer Catalysts.

Nii et al.; *Tetrahedron Letters,* 27, pp. 2517–2520 (1979), Synthesis of Amidinoformic Acids Using Benzyl Cyanoformate as a Synthon.

*Primary Examiner*—Joseph Paul Brust
*Attorney, Agent, or Firm*—Bruce J. Barclay; Arthur R. Whale

[57] ABSTRACT

A process for preparing a $C_3$–$C_8$ alkyl cyanoformate derivative employing a liquid-liquid phase transfer catalysis conducted at low temperatures.

5 Claims, No Drawings

PROCESS FOR PREPARING CEPHALOSPORIN INTERMEDIATES

This application is a continuation of application Ser. No. 534,467, filed Sept. 21, 1983, now abandoned.

SUMMARY OF THE INVENTION

The present invention relates to a process for preparing a $C_3$-$C_8$ alkyl cyanoformate comprising reacting about 1.0 equivalent of a $C_3$-$C_8$ alkyl haloformate in a suitable solvent with about 1.0 to 1.5 equivalents of an alkali metal cyanide in the presence of water and a catalytically sufficient amount of a quaternary ammonium phase transfer catalyst at a temperature in the range of from about 0° C. to −30° C.

The present process has been found to economically produce large quantities of $C_3$-$C_8$ alkyl cyanoformate derivatives in very high yields and to provide the product consistently with high purity without the need for additional expensive purification steps. The use of water in the present process allows for the efficiency of a liquid-liquid phase transfer catalysis. Also, the $C_3$-$C_8$ haloformate derivatives, for example, are readily available and inexpensive starting materials employed in the present process. Several other advantages of the present process are outlined below.

DETAILED DESCRIPTION OF THE INVENTION

The term $C_3$-$C_8$ alkyl represents a straight or branched alkyl chain having from three to eight carbon atoms. Typical $C_3$-$C_8$ alkyl groups include n-propyl, isopropyl, n-butyl, isobutyl, sec.-butyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, 2-ethylhexyl and the like.

The terms halo or halogen, as defined herein, represent fluoro, chloro, bromo and iodo. Bromo, and especially chloro, are preferred.

While the entire scope of process variables taught herein are believed advantageous, the present process does have preferred aspects. Preferably the $C_3$-$C_8$ alkyl cyanoformate is isobutyl cyanoformate and the preferred $C_3$-$C_8$ alkyl haloformate is isobutyl chloroformate. Other preferred process conditions will be noted hereinafter.

The $C_3$-$C_8$ alkyl cyanoformate prepared by the present process is reacted with an alkyl azidoacetate to provide a 5-($C_3$-$C_8$ alkoxycarbonyl)-1H-tetrazole-1-acetic acid ester. The 5-($C_3$-$C_8$ alkoxycarbonyl)-1H-tetrazole-1-acetic acid esters thus prepared have a variety of uses, but are preferably used as intermediates to the corresponding compound 1H-tetrazole-1-acetic acid, which is used as an intermediate in the production of certain cephalosporin compounds as described in U.S. Pat. No. 3,516,997.

The process of the present invention is generally performed as follows. Approximately 1.0 equivalent of a $C_3$-$C_8$ alkyl haloformate is added to a stirred solution of a halogenated hydrocarbon solvent, such as chloroform and especially methylene chloride, and a catalytically sufficient amount of a quaternary ammonium phase transfer catalyst cooled to about 0° C. to about −70° C. with external cooling. The term "catalytically sufficient amount", as defined herein, refers to an amount of a quaternary ammonium phase transfer catalyst which is capable of increasing the rate of the chemical reaction. This amount is typically relatively small in comparison to the quantity of reactants, for example, at a concentration in the range of from about 0.01% to about 5% of catalyst per equivalent of $C_3$-$C_8$ alkyl haloformate. The preferred quaternary ammonium phase transfer catalysts are Aliquat 336 (tricaprylylmethylammonium chloride from Henkel Corp., Tucson, Ariz.), and Adogen 464 (methyltrialky($C_8$-$C_{10}$)-ammonium chloride from Aldrich Chemical Co., Milwaukee, Wis.) and their use is described in U.S. Pat. No. 3,992,432. A review of quaternary ammonium phase transfer catalysts in general may be found in *Aldrichimica Acta*, 9, 35 (1976).

After the solution has cooled to a temperature in the range of about 0° C. to −30° C., more preferably to about −5° C. to −25° C., water, preferably in the form of ice, is added to the reaction mixture. The water phase permits the use of a more efficient liquid-liquid phase transfer, but its use makes the reaction exothermic. Therefore, as an internal heat sink to control the exotherm, a suitable means of internal cooling such as crushed ice is preferably added to the stirring solution to generally provide a thick slurry of reactants. Another suitable means of internal cooling is a coil which is simply immersed in the reaction mixture. As the heat of reaction melts the ice, the water phase is created. While maintaining the temperature of the reaction mixture at about 0° C. to −30° C., approximately from 1.0 to 1.5 equivalents of an alkali metal cyanide is generally added to the reaction mixture. Typical alkali metal cyanide reagents are potassium, lithium and especially sodium cyanide.

The $C_3$-$C_8$ alkyl haloformate is preferably added to the reaction mixture before the addition of the alkali metal cyanide, but may also be added after the addition of the cyanide reagent. In this instance the ice slurry is formed by externally cooling with dry ice/acetone, for example, an emulsion of the aqueous reaction mixture containing the alkali metal cyanide in water and the halogenated hydrocarbon solvent.

When the alkali metal cyanide is added last to the reaction mixture, within one to two minutes the reaction temperature drops to about −18° C. When the $C_3$-$C_8$ alkyl haloformate is added last, the reaction commences upon the melting of the solid-aqueous phase at around −25° C. to −30° C. Approximately 10 to 20 minutes thereafter the temperature has risen to about −20° C. to −2° C. due to the heat of the reaction. However, the external cooling bath surrounding the reaction vessel should remain at a temperature less than approximately −8° C. to −10° C. throughout the process of the present invention. After the reaction mixture has stirred for approximately 30 to 35 minutes, the temperature of the reaction mixture drops again under the influence of the external cooling bath. At this point, the reaction is complete and the product in the organic phase is separated. Since the product is prone to hydrolytic decomposition, it is necessary for the operator to work quickly and keep the solutions cold. The lower organic layer containing the $C_3$-$C_8$ alkyl cyanoformate, phase transfer catalyst and solvent is removed and kept cold. The upper aqueous layer is quickly extracted with a water immiscible organic solvent and the extracts combined with the product layer. The upper layer is then generally discarded.

The product layer is preferably purified by adding an anhydrous drying agent, such as silica, to the solution so as to absorb the catalyst and any residual water. For example, the solution may be stirred with silica at a reduced temperature such as 0° C. for approximately 30 to 45 minutes. The silica is subsequently removed by filtration and may be either discarded or saved and regenerated by washing it with methanol and drying.

Due to its mild conditions, another advantage of the present process is that the cyanoformate may also be formed in the presence of the alkyl azidoacetate, which acts as a cosolvent for the reaction, and the present process is preferably so conducted. At lower temperatures the alkyl azidoacetate and the alkyl cyanoformate do not react. The two reactants may be subsequently heated as described below to provide the 5-($C_3$–$C_8$ alkoxycarbonyl)-1H-tetrazole-1-acetic acid ester. When the alkyl azidoacetate is present in the reaction mixture, a proportionally lesser amount of solvent and catalyst are required than when the azidoacetate is absent. However, when the solution containing the $C_3$–$C_8$ alkyl cyanoformate contains only solvent and none of the alkyl azidoacetate, the cyanoformate may be isolated and the solvent may be recovered by fractional distillation as the product is much higher boiling than the solvent employed in the reaction.

As noted above, the $C_3$–$C_8$ alkyl cyanoformate prepared by the process of the present invention is preferably used as an intermediate to the production of 1H-tetrazole-1-acetic acid. This synthesis has been carried out by Katner in U.S. Pat. No. 3,962,272. However, several advantages exist in using a $C_3$–$C_8$ alkyl cyanoformate in the synthesis of 1H-tetrazole-1-acetic acid. The use of a $C_3$–$C_8$ alkyl cyanoformate in the production of the acetic acid has an added safety factor in that it has a lower vapor pressure than the corresponding methyl or ethyl cyanoformate analogs thereby reducing the occurrence of toxic fumes. The higher boiling point is also advantageous for achieving the desired reaction temperature in the preparation of the 5-($C_3$–$C_8$ alkoxycarbonyl)-1H-tetrazole-1-acetic acid ester. Another advantage of using a $C_3$–$C_8$ alkyl cyanoformate over lower alkyl cyanoformates is its lower water solubility and therefore reduced likelihood of loss to the aqueous layer in the work up of the reaction mixture of the present process.

The $C_3$–$C_8$ alkyl cyanoformate thus formed by the present process is preferably used in the preparation of the 5-($C_3$–$C_8$ alkoxycarbonyl)-1H-tetrazole-1-acetic acid ester. This reaction is preferably carried out by combining one equivalent of the alkyl azidoacetate with from one to three equivalents of $C_3$–$C_8$ alkyl cyanoformate. A halogenated hydrocarbon solvent, such as methylene chloride, may also be present in the reaction mixture but is not necessary. The reaction is substantially complete after about 14 to 24 hours when carried out at a temperature in the range of from about 125° to 140° C.

After the product has formed, any excess $C_3$–$C_8$ alkyl cyanoformate used in the reaction may be recovered by distilling off the reactant under vacuum. Therefore, since the excess $C_3$–$C_8$ alkyl cyanoformate may be recovered following formation of the product, the quantity of the reactant in excess of one equivalent is not critical. Having distilled off all of the reactants, substantially pure product remains which may then be directly hydrolyzed to the acetic acid.

The compound thus prepared is next hydrolyzed and decarboxylated to 1H-tetrazole-1-acetic acid by procedures well known to those skilled in the art. This procedure is carried out by combining the 5-($C_3$–$C_8$ alkoxycarbonyl)-1H-tetrazole-1-acetic acid ester with 1.0 to 1.5 equivalents of a suitable aqueous mineral acid. Suitable acids include hydrofluoric, hydrobromic and especially hydrochloric acid. Preferably, the reaction mixture is heated to reflux with stirring and the alcohols that are liberated by the ester hydrolysis are advantageously distilled out. As the alcohols are distilled away, water should be added to the reaction mixture to maintain the original volume. Completion of this reaction is signalled by the cessation of carbon dioxide evolution, which typically takes from 4 to 6 hours.

The 1H-tetrazole-1-acetic acid thus formed may be purified by any one of several well known procedures, but is preferably purified as follows. Generally, the reaction mixture is cooled to about 90° C. and a small quantity of nitric acid is added to the mixture. The mixture is stirred at 80° C. and a small quantity of decolorizing charcoal is added to the solution. The mixture is filtered hot through a Celite cake. The filtrate is slowly cooled and seeded with a crystal of the product. The product thus formed is collected by filtration. The acidic mother liquor may be added to a subsequent hydrolysis reaction for recovery of additional material. Eventually, the mother liquor is discarded because of an excess of accumulated salts.

The process of the present invention is further illustrated by the following Examples. The compounds prepared below were characterized as peaks on the gas chromatograph and compared to a reference standard. The instrument used was a Hewlet-Packard #5700, with a thermal conductivity detector. The column was 5 ft. long by 4 mm ID glass, packed with 60–80 mesh Chrom G, coated with 4% (wt) XE60. The carrier gas was helium, and the rate 60 ml./min. For assaying the starting azidoacetate and cyanoformate esters the column was typically run at either 50° C. or 100° C. For assaying the tetrazole ester derivatives a column temperature of 200° C. was required. All compounds can be assayed in the same run by programming the temperature to start at 50° C. (held for 2 minutes) and then to rise to 230° C. at 32°/min.

Example 1

Preparation of 2-ethylhexyl cyanoformate

A solution of 600 ml. of methylene chloride and 4 grams (0.01 moles) of Aliquat 336 was charged into a 2 l. 3-neck round bottom flask and cooled to approximately −60° C. with a dry ice/acetone bath. An aqueous solution of 120 grams (2.45 moles) of sodium cyanide in 250 ml. of water was added dropwise to the reaction mixture to provide a slurry of reactants. Next, 385.38 grams (2.0 moles) of 2-ethylhexyl chloroformate was added to the mixture while maintaining the temperature below approximately −40° C. The external cooling was then removed from the reaction flask and the mixture was allowed to warm slowly. After 19 minutes the mixture had warmed to −25° C. and the external cooling was replaced. After 9 more minutes the temperature of the reaction mixture was −17° C. at which point 100 ml. of water, 200 ml. of carbon tetrachloride and 100 ml. of ice was added and the layers were allowed to separate. The organic phase was separated, and the aqueous phase was extracted twice with methylene chloride. The organic extracts were combined and dried over anhydrous magnesium sulfate. The organic phase was concentrated under reduced pressure and the residue was distilled under vacuum to provide 347.85 grams of 99.7% pure 2-ethylhexyl cyanoformate (94.9% yield). bp=95° C. (12-15 mm).

EXAMPLE 2

Production of 1H-tetrazole-1-acetic acid

A. Preparation of ethyl azidoacetate

A solution of 55.7 grams (0.45 moles) of 99% pure ethyl chloroacetate (Aldrich Chemical Company, Milwaukee, Wis.), 0.64 grams (1.6 millimoles) of Aliquat 336 and 30.16 grams (0.46 moles) of sodium azide (Aldrich) in 50 ml. of methylene chloride and 50 ml. of water was heated to reflux for 16 hours in a 250 ml. round bottom 3-neck flask. The mixture was allowed to cool, whereupon an additional 30 ml. of water was added to dissolve the precipitated sodium chloride. The organic phase was separated and the aqueous phase was washed twice with 10 ml. aliquots of methylene chloride. The aqueous phase was discarded and the organic phases were combined and used as a solvent for the following reaction.

B. Preparation of isobutyl cyanoformate

The solution prepared in part A containing ethyl azidoacetate/Aliquat 336/methylene chloride totaling approximately 120 ml. in volume was cooled to approximately $-5°$ C. in a 500 ml. round bottom 3-neck flask. When the solution reached $-5°$ C., 69 grams (0.50 moles) of 99% pure isobutyl chloroformate (Aldrich) was added to the reaction mixture. The mixture was again allowed to cool to $-5°$ C. whereupon 150 grams of crushed ice was next added to the well stirred reaction mixture. While maintaining the temperature of the reaction mixture at $-5°$ C., 26.91 grams (0.55 moles) of sodium cyanide was added. After 30 minutes the phases were separated and the upper aqueous layer was washed twice with 5 ml. portions of methylene chloride and discarded. The methylene chloride extracts and separated organic phase were combined and stirred with silica gel at 0° C. for approximately 30 minutes. The mixture was filtered and the residue washed three times with 10 ml. aliquots of methylene chloride. The filtrate was returned to a 250 ml. round bottom 3-neck flask and distilled to recover approximately 110 ml. of methylene chloride.

C. Preparation of 5-(isobutoxycarbonyl)-1H-tetrazole-1-acetic acid, ethyl ester As room became available in the round bottom flask during the recovery process of methylene chloride, an excess of isobutyl cyanoformate (62.42 grams, 0.46 moles) prepared in a separate reaction similar to the process described in Example 1 was added to the mixture. The reaction mixture was then heated to 130° C. for approximately 19½ hours. The solution was next distilled in vacuo to recover 60.59 grams of excess isobutyl cyanoformate (91.1% pure cyanoformate by gas chromatography). The residual liquid product was allowed to cool to approximately 100° C. while maintaining the vacuum and was used directly in the following reaction.

D. Preparation of 1H-tetrazole-1-acetic acid

The crude 5-(isobutoxycarbonyl)-1H-tetrazole-1-acetic acid, ethyl ester prepared above was treated with 37.5 ml. (0.45 moles) of concentrated hydrochloric acid and 37.5 ml. of water in a 250 ml. 3-neck round bottom flask. The reaction mixture was heated to reflux, and the alcohols liberated as by-products of the reaction were allowed to distill out and carbon dioxide was permitted to evolve. Water was added as required during the reaction to maintain the volume in the flask at approximately 110 ml. When the distillation of the alcohols had ended, the mixture was treated with approximately 1 ml. of nitric acid to decolorize the solution. The solution was then cooled to approximately 70° C. and treated with charcoal. The solution was stirred for approximately 20 minutes and filtered hot into a clean 250 ml. 3-neck round bottom flask, washing with a minimum of water. The volume of the solution was reduced to approximately 120 ml. by distillation in vacuo and the mixture cooled. The precipitated solid was collected by filtration to afford 46.48 grams (98.1% pure) of 1H-tetrazole-1-acetic acid (m.p. 128.5°–130° C.). The overall yield of the synthesis from ethyl chloroacetate was 80.6% in the first cycle. When the 1H-tetrazole-1-acetic acid mother liquor was used as the solvent for the hydrolysis reaction in subsequent batches, the average yield of product over 9 cycles was 93.1%, with an average assay of 98.5% purity. The mother liquor was discarded after 9 cycles due to the salt accumulation.

I claim:

1. A process for preparing a $C_3$–$C_8$ alkyl cyanoformate comprising reacting about 1.0 equivalent of a $C_3$–$C_8$ alkyl haloformate in a suitable solvent with about 1.0 to 1.5 equivalents of an alkali metal cyanide in the presence of water and a catalytically sufficient amount of a quaternary ammonium phase transfer catalyst at a temperature in the range of from about 31 5° C. to about $-25°$ C.

2. The process of claim 1 wherein the $C_3$–$C_8$ alkyl haloformate is isobutyl chloroformate and the $C_3$–$C_8$ alkyl cyanoformate is isobutyl cyanoformate.

3. The process of claim 2 wherein the alkali metal cyanide is sodium cyanide.

4. The process of claim 1 wherein the quaternary ammonium phase transfer catalyst is tricaprylylmethylammonium chloride.

5. The process of claim 1 wherein the quaternary ammonium phase transfer catalyst is a methyltrialkyl-($C_8$–$C_{10}$)-ammonium chloride.

* * * * *

UNITED STATES PATENT AND TRADEMARK OFFICE
CERTIFICATE OF CORRECTION

PATENT NO. : 4,539,422

DATED : September 3, 1985

INVENTOR(S) : Ian G. Wright

It is certified that error appears in the above—identified patent and that said Letters Patent is hereby corrected as shown below:

Column 6, line 44, "315°C." should read -- -5°C. --.

Signed and Sealed this

Twenty-first Day of January 1986

[SEAL]

Attest:

DONALD J. QUIGG

Attesting Officer

Commissioner of Patents and Trademarks